US007767150B1

(12) United States Patent
Zaromb et al.

(10) Patent No.: US 7,767,150 B1
(45) Date of Patent: *Aug. 3, 2010

(54) AEROSOL COLLECTION APPARATUS AND METHODS

(76) Inventors: Solomon Zaromb, 9S 706 William Dr., Burr Ridge, IL (US) 60527; Dennis J. Martell, 7 Cider Hill La., Douglas, MI (US) 49406; Isaac Ray, 35 Sea Coast Ter., Apt 11R, Brooklyn, NY (US) 11235

( * ) Notice: Subject to any disclaimer, the term of this patent is extended or adjusted under 35 U.S.C. 154(b) by 1301 days.

This patent is subject to a terminal disclaimer.

(21) Appl. No.: 10/710,838

(22) Filed: Aug. 5, 2004

Related U.S. Application Data

(60) Provisional application No. 60/481,184, filed on Aug. 6, 2003.

(51) Int. Cl.
*B01L 3/00* (2006.01)
(52) U.S. Cl. ....................................... 422/99
(58) Field of Classification Search ............... 422/99
See application file for complete search history.

(56) References Cited

U.S. PATENT DOCUMENTS

| | | | | | |
|---|---|---|---|---|---|
| 2,916,626 | A | * | 12/1959 | Thomas et al. ............ | 250/375 |
| 2,932,966 | A | * | 4/1960 | Grindell .................... | 73/23.31 |
| 3,561,444 | A | * | 2/1971 | Boucher ................ | 128/200.16 |
| 3,765,154 | A | * | 10/1973 | Hardt et al. ............... | 96/88 |
| 5,085,673 | A | * | 2/1992 | Bentley et al. ............. | 95/29 |
| 5,173,264 | A | * | 12/1992 | Zaromb et al. ............ | 422/88 |
| 5,855,652 | A | * | 1/1999 | Talley ....................... | 96/44 |
| 6,221,136 | B1 | * | 4/2001 | Liu et al. ................... | 96/66 |

* cited by examiner

*Primary Examiner*—Walter D Griffin
*Assistant Examiner*—Bobby Ramdhanie

(57) ABSTRACT

Apparatus and methods for detecting the presence of an airborne chemical or biological analyte utilise:a substantially gas- and liquid-impermeable container; means for introducing a substantially analyte-free collection liquid into said container; means for rapidly sampling ambient air and transferring said analyte therefrom into said collection liquid, said sampling means comprising an air intake means and and an air venting means; and-means for removing from said container an analyte-enriched collection liquid; wherein said volume of air passes through a substantially horizontal air inlet and upwardly through a substantially vertical collector electrode tube with means for applying an electric field between said tube and a co-axial spiked wire- or rod-shaped discharge electrode.

20 Claims, 3 Drawing Sheets

PRIOR ART

AEROSOL COLLECTION APPARATUS AND METHODS

CROSS REFERENCE TO RELATED APPLICATIONS

This is a non-provisional application of provisional application number 60/481,184, filed Aug. 6, 2003, which is related to my U.S. Pat. No. 5,328,851, 6,087,183, and 6,565,811 and to its U.S. patent applications Ser. Nos. 08/377,966 [filed Jan. 25, 1995] and 09/611,744 [filed Jul. 7, 2000] now U.S. Pat. Nos. 6,762,068B1 and 6,642,057B1. The disclosures of all of said applications and patents are incorporated herein by reference."

BACKGROUND OF INVENTION

This invention relates to improved apparatus and methods for detecting harmful substances, whether airborne or grounded, whether biological or chemical, which may pose an immediate or long term hazard to human life or health.

The afore-cited patents and co-pending applications, disclose apparatus and methods for collecting various contaminants—including vapors and particles, chemical or biological—from a large volume of air into a small volume of carrier liquid, so as to permit or facilitate rapid and ultra-sensitive detection of traces of hazardous or illicit substances which may be otherwise difficult to detect. The collected contaminants may be either dissolved by or suspended in the carrier liquid.

The earliest apparatus of this type was intended mainly for the absorption of vapors by the carrier liquid and was therefore referred to as liquid-absorption air sampler. With subsequent use of the same apparatus for the collection of respirable particles, the term "absorption" became inappropriate, as the collected particles may remain suspended in the carrier liquid without being dissolved therein. Such apparatus and methods will therefore be referred to herein as "HTLAAS" for High-Throughput Liquid-Assisted Air Sampling, which applies to collected air contaminants which are either dissolved or suspended in a carrier liquid.

A good measure of the performance of HTLAAS devices is the concentration factor F, which is proportional to the ratio of the concentrations in the liquid carrier and in air of the monitored air contaminant, hereinafter referred to as "analyte." The concentration factor F is defined by the equation $F=\epsilon S/v_L$[1], where $\epsilon$ is the sampler's collection efficiency, S is its air sampling rate, and $v_L$ is the volume of liquid in which the analyte is collected. The concentration factor F can thus be enhanced by increasing $\epsilon$ and/or S or by decreasing $v_L$.

The need for efficient aerosol collectors has been appreciated for more than a decade both for all point bio-detection systems and for future chemical point detectors, and several collectors have been developed and used by the military and first responders. However, recent incidents of bio-terrorisms have revealed serous shortcomings of these collectors. When these were used in conjunction with immunoassay-based test strips, the resulting effective detection limit for anthrax bacilli was far above the known dangerous or lethal concentrations, so that inhalation of low but lethal doses of anthrax or other biological warfare [BW] aerosol agents could have been easily overlooked. Although several existing wetted wall cyclone aerosol collectors can remove a substantial fraction of particulates from a large volume of air (several cubic meters) and transfer them into a small liquid volume (a few milliliters) for analysis, their power requirements are high (400-500 watts)—driven by the need to collect particles as small as 1 micron. Cyclones and most inertial separation devices are intrinsically very inefficient at capturing small particles.

Somewhat of an exception may be the PHTLAAS [Portable HTLAAS] of U.S. Pat. No. 6,087,183, a variant of which was found to yield a collection efficiency of 66±3% for 1-micron particles and 84±4% for 4-micron particles at an air flow rate of 317 liters/minutes, as reported by Kessvan, J.; Carlile, D.; Doherty, R. W.; Sutton, T.; and Hottell, A.; "CHARACTERISTICS AND SAMPLING EFFICIENCY OF PHTLASS™ AIR SAMPLER," ECBC-TR-267, 2002. When a similar sampler, hereafter referred to as "recent PHTLAAS" [FIG. 1], was operated at full power with a 12-volt battery, the measured power consumption was only 42 watts [3.5 amps at 12 volts]. The comparatively low power consumption of only 42 watts by the recent PHTLAAS is attributed to its patented unique flow pattern in which the direction of the air stream is partly reversed as it enters through the air intake, as disclosed in U.S. Pat. No. 6,087,183.

Although this recent PHTLAAS seems to compare favorably with other inertial-separation-type collectors, it still cannot match the much higher efficiencies that are obtainable with electrostatic precipitation [EP] technology for removing small particles from a gas [see, e.g., Altman, R.; Beckley, W.; and Ray, I.; "WET ELECTROSTATIC PRECIPITATION DEMONSTRATING PROMISE FOR FINE PARTICULATE CONTROL," Power Engineering, January-February, 2001, or Parker, K. R., editor; "Applied Electrostatic Precipitation," Chapman & Hall, London, 1997].

According to the latter references, wet EP can achieve collection efficiencies of 99.9% for particles as small as 0.01 micron in size and for various gaseous species, including dioxins/furans, which could also assure capture of toxins and dry virus particles. The latter remain suspended in air long after evaporation of water from the droplets in which they were originally dispersed and may thus present a persistent not readily noticeable hazard. Therefore, an ability to collect dry virus particles should greatly enhance the effectiveness of biological agent detection systems.

Inertial separation devices, including the PHTLAAS, operate on altogether different principles than EP and consequently have different physical structures. Whereas the airflow within the recent PHTLAAS is highly turbulent and swirling rapidly, so as to Impel particles towards the container wall by centripetal action, the flow in EP devices is substantially laminar, so as to permit high flow rates at rather low pressure drops and low power consumption.

The major reduction in power consumption that is expected from the use of EP yields not only major savings in the size, operating costs, and equipment cost of the resulting collectors, but also smaller and lighter instruments by reducing the size and weight of required batteries or else permits uninterrupted operation between battery replacements for longer time periods, thereby further increasing the utility of portable collectors.

SUMMARY OF INVENTION

In spite of their altogether different and maybe even incompatible basic operating principles and consequent differences between inertial and EP-based devices, it is an object of the present invention to provide PHTLAAS-EP apparatus and methods yielding improvements that would not be expected from either of these technologies alone.

It is an object of this invention to incorporate EP within the present PHTLAAS configuration with relatively minor modifications.

It is another object to effectuate modifications that permit an EP-activated PHTLAAS to operate either as a continuous wet precipitator or as an alternating intermittent dry and wet precipitation device so as to result in a transfer of precipitated particles into a small volume of collection fluid.

It is an overall objective of the present invention to provide new aerosol collector devices which maximize the quantity of aerosol collected in the size range of 1-10 microns while also reducing overall equipment size, weight, cost and power requirements.

It is an object of the invention to provide an EP-based aerosol collection system sampling air at a high rate, e.g., >500 l/min, and capturing particles throughout the size range of 1-10 microns at a collection efficiency of >80%.

It is a further object of the invention to increase the collection efficiency and air sampling rate while reducing the power requirements and volume of the collection medium [water or an aqueous solution].

Other objects of our invention are to provide an electronically programmable interface between a collector and a detector, so as to yield an automated or quasi-automated collection-detection system, to reduce the size and weight of the overall system, and to further enhance the system's sensitivity by further increasing its collection efficiency and air sampling rate.

More objects of the invention will become apparent to professionals in the chemical and biological defense, law enforcement, health monitoring, disease control, industrial safety and hygiene, environmental, chemical, metallurgical, and related areas following perusal of the complete specification.

Briefly, the invention consists of effectuating modifications in the basic configuration of the PHTLAAS of Pat. No. 6,565,811 so as to convert it into an EP-based air sampler. These modifications consist of replacing the glass sampling tube of the PHTLAAS by an electrically conductive collector electrode tube, inserting a wire- or rod-shaped high-voltage discharge electrode co-axially with the collector electrode, and modifying the air intake so that it is designed and disposed to yield a high air flow through the sampler at a low pressure drop and low power consumption. Upon turning on the power, sampled air is now drawn in through the modified intake and caused to flow upward through the collector tube. Also drawn in through that intake is a fine mist of water droplets preferably generated by an ultrasonic humidifier yielding a liquid film on the inner surface of the collector electrode for either maintaining continuous full collector electrode wetting in a wet EP system [WEP] or for removal of captured particles from the collector wall at appropriate intervals in a dry EP system, such removal being aided by ultrasonic waves transmitted through the collector tube.

BRIEF DESCRIPTION OF DRAWINGS

The invention is best explained with reference to the drawings, in which.

DETAILED DESCRIPTION

Since inertial separation and EP operate on different physical principles, the two approaches would not be expected to share many common features. Nevertheless, the collector electrode in a cylindrical EP system bears a physical resemblance to the glass sampling tube of the recent PHTLAAS, and the latter's liquid wash-down and collection scheme is directly applicable to EP.

Figure 1:
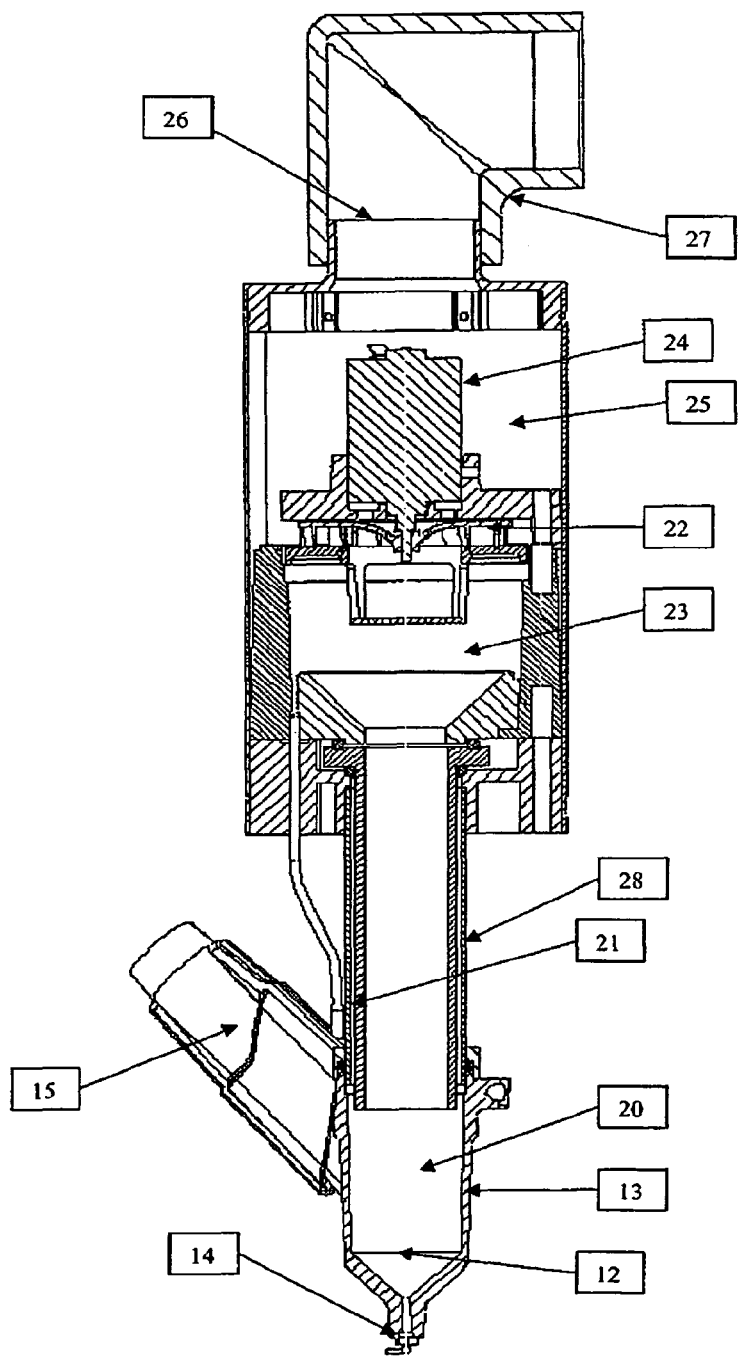
FIG. 1 is a view of the recent PHTLAAS mainly in vertical cross-section and partly in elevation.

FIG. 1 shows the main components of a recent PHTLAAS, which include a slanted air intake 15 forming an integral part of a liquid supply and collection compartment 13, a flanged glass air sampling tube 21, an upper expansion chamber 23 leading to an air exhaust compartment 25, which includes a centrifugal blower 22 driven by a motor 24 and an air outlet opening 26 capped by a flow deflecting elbow 27. In operation, with blower 22 turned on, sampled air is drawn through inlet 15 into a lower cylindrical chamber 20 and thence through the sampling tube 21 and upper expansion chamber 23 into blower 22, whence it is expelled through opening 26 and elbow 27. Part of the air entering the lower chamber 20 impinges upon a collection liquid 12 at a funnel-shaped bottom of that chamber, thereby generating a mist of entrained droplets which form a liquid film over the inner surface of sampling tube 21.

Figure 2:
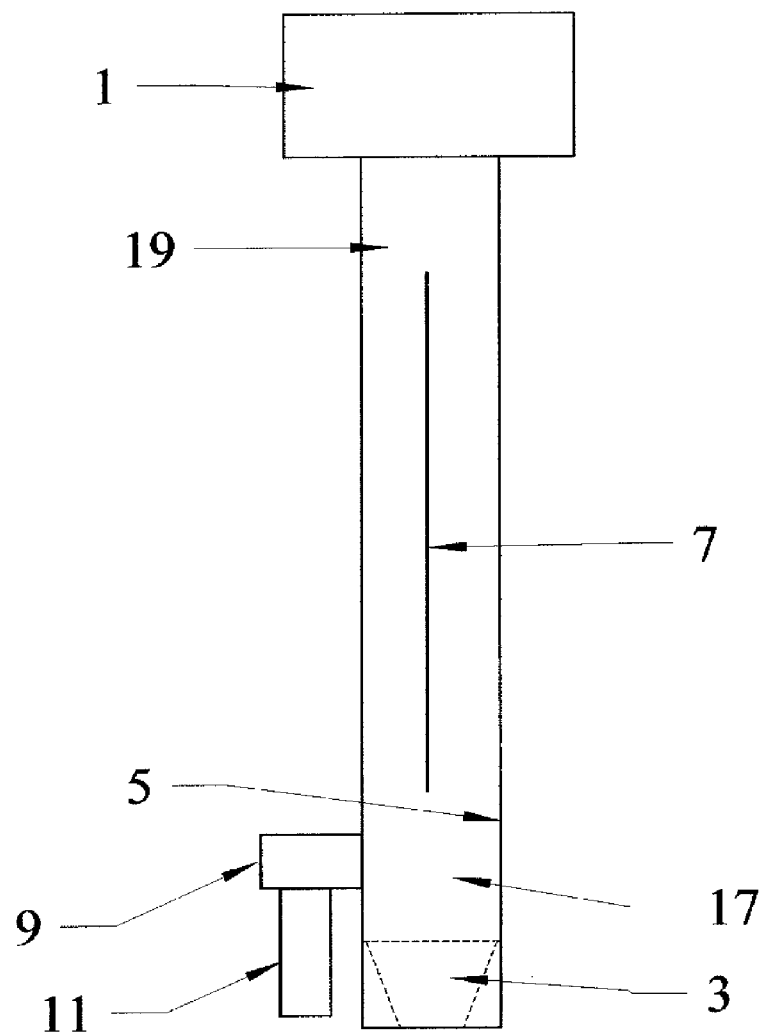
FIG. 2 is a schematic block diagram of a PHTLAAS-EP system.

An outlet nipple 14 at the bottom of compartment 13, usually closed off, permits drainage or withdrawal of collection liquid 12 into a bottle, syringe or other storage container or appropriate chemical or biological sensor device, The modifications in the recent PHTLAAS configuration that would be required to yield an EP-activated device, referred to hereafter as PHTLAAS-EP, are indicated schematically in FIG. 2.

Of the components shown in FIG. 2, the topmost air exhaust 1 and the lowermost liquid collection and removal system 3 can be substantially the same as or similar to the same components 22-27 and 12-14, respectively, in the recent PHTLAAS of FIG. 1. The collector electrode 5 can be similar to the sampling tube 21 of FIG. 1 but with its inner surface electrically conducting. The main altogether new components are the central wire-or red-shaped discharge electrode 7, kept at a high negative or positive potential [possibly of as much as 10 KV or higher], and a horizontal tubular EP air intake 9, through which air can enter unimpeded at a high flow rate with a minimal pressure drop.

As in the recent PHTLAAS, a mist that is carried up with the sampled air stream deposits on the inner surface of the collector electrode 7 and forms a wetted film thereon. However, collection of small aerosol particles is effected by corona discharge from the central electrode 7 generating ionized particles which are driven towards collector electrode 5 by an electric field.

For this scheme to work optimally, the following factors need to be ascertained: 1) Controllable Mist Formation. To prevent collection losses due to captured particles adhering to the collector electrode, it is essential that the entire inner surface of the tubular electrode be covered by a liquid film at least 25 microns thick. This can be best assured by having liquid dripping from the top down a roughened [sandblasted] stainless steel surface and supplemented by liquid droplets that are carried upward by the sampled air. To reduce the average size of these droplets to only a few microns and assure an evenly distributed airflow through the tubular electrode, two perforated baffles or screens are inserted above the air intake. The baffles have openings of about ⅛"and an open area of at least 40% so as to generate a pressure drop of not more than ½"of water.

The performance of the WEP is strongly dependent on the ratio of liquid and gas flows and on the size of the droplets. A preferred wetting approach is to generate a water mist ultrasonically near the sampler inlet and let the inrushing air carry the mist with it. After operating a Reli ON® Model H-0565-0 30-watt 2-gallons/day [5 ml/minute] ultrasonic humidifier near the 1.5" intake opening and adjusting the flow rate to about 600 l/min, we achieved full wetting of the 2" ID tube starting from the lower portion and extending through its 18" length within a few minutes even without applying a high voltage between the collector and discharge electrodes. With EP, the droplets get charged and carried rapidly towards the well, which speeds up the wetting process.

The ultrasonically generated mist offers an acceptable combination of fine droplet size, uniformity of droplets distribution, and modest power consumption for the required humidification rate. The Reli On® Model H-0565-0 ultrasonic humidifier was found to yield humidlfation rates: of 2.8, 3.7, and 5.9 ml/min for power drains of 12, 15, and 20 watts, respectively. With maximum power requirements of 20 watts for sonification, 6 watts for electrostatic precipitation, and <10 watts for the air blower, the total power consumption adds up to <40 watts for an air sampling rate of >500 liters/minute.

However, some fine-tuning is required to assure that the generated mist is sufficient to result in proper wetting of the collector electrode and yet not so high as to cause unwanted spark discharges. Such tuning can be effected by adjusting the power of the exhaust air blower and the inter-electrode voltage and electric field distribution.

Proper Operation of the EP Electrodes. To assure collection of at least 80% of particles 1-10 microns in size at an airflow rate of at least 500 l/min, the electrodes and applied voltage must be designed and adjusted so as to generate a sufficient corona to ionize most of the particles in the air stream and a sufficient electric field to deposit most of these particles at the collector electrode. The latter's length and diameter must be such as to allow an adequate residence time for most particles to reach it rather than be carried away with the air stream.

The performance with negative and positive discharge electrode voltages can be compared with a view to minimizing undesirable ozone formation and spark discharges. Ozone formation, which kills bacteria and thereby interferes with their detection and concentration measurements by colony counts, can be minimized by using positive rather than negative discharge electrode voltages, but this may also result in increased spark discharges unless prevented by careful adjustment of the electric field.

Operation in a Continuously Wetted Mode or an Alternating Intermittent Dry and Wet Mode. Operation in an alternating dry and wet mode cuts down on evaporation losses during the dry periods and thus reduces the water replenishment requirements. It also limits the occurrence of any possible power losses due to spark discharges to the relatively brief wet wash-down periods. However, the mode switching and its proper timing complicate the design and operation of the system and hence its equipment and maintenance costs. There is also a possibility of some dried biological agents tending to stick to the collector wall and not being easily washed down during the wet period. Removal of the sticking particles can be helped by generating and transmitting ultrasonic waves across the interface between the collector electrode and the liquid film covering its inner surface.

The preceding discussion outlines the basic features of the PHTLAAS-EP system of this invention.

As mentioned above, the recent inertial-type PHTLAAS comes close to meeting requirements for an aerosol collection system sampling air at a rate of at least 500 l/min and capturing particles throughout the size range of 1-10 microns at a collection efficiency of at least 80%. However, a major gain in energy efficiency is achieved with an EP-based system by replacing the slanted intake 15 [FIG. 1] by a horizontal radially directed low-pressure-drop air intake 9 [FIG. 2] and adjusting the airflow rate therethrough to above 500 l/min with minimal blower power; replacing the glass sampling tube of the recent PHTLAAS by a grounded tubular collector electrode; and inserting an axial discharge electrode, with these electrodes connected to opposite terminals of a high-voltage power supply. These modifications are detailed as follows:

Modification 1: To provide an EP air intake, a sizable radial hole, preferably <1", is made in the lower tubular container 13 of the PHTLAAS of FIG. 1 and a straight tubular inlet 9 of the same outer diameter is threaded or otherwise fitted into it. Intake 9 replaces and differs in two major ways from the slanted intake 15 of FIG. 1. Intake 9 is not only horizontal as in FIG. 2, but it also directs the air into chamber 17 first radially towards the axis and then linearly upward, so as to minimize resistance to airflow. Therefore, the power needed to draw air through intake 9 is far lower than what would be required to achieve a comparable flow rate through the replaced inlet 15. The power, i.e., voltage and current, fed to the air blower 22 of FIG. 1 can then be adjusted to higher flow rates through intake 9.

Modification 2: To provide the collector electrode 5 of FIG. 2, an electrically conductive coating or foil may be applied to the inner surface 23 and flange 25 of the flanged glass sampling tube 27 of the PHTLAAS of FIG. 1. The conductive-coated flange of the collector electrode tube may be connected through a pressure contact to an electrically conductive washer, made of a resilient electrically conductive polymer, and hence to the ground terminal of a high-voltage power supply [not shown]. Alternatively, the glass sampling tube 21 with its protective outer tube 28 may be replaced by a thin metallic tube 5.

Figure 3:
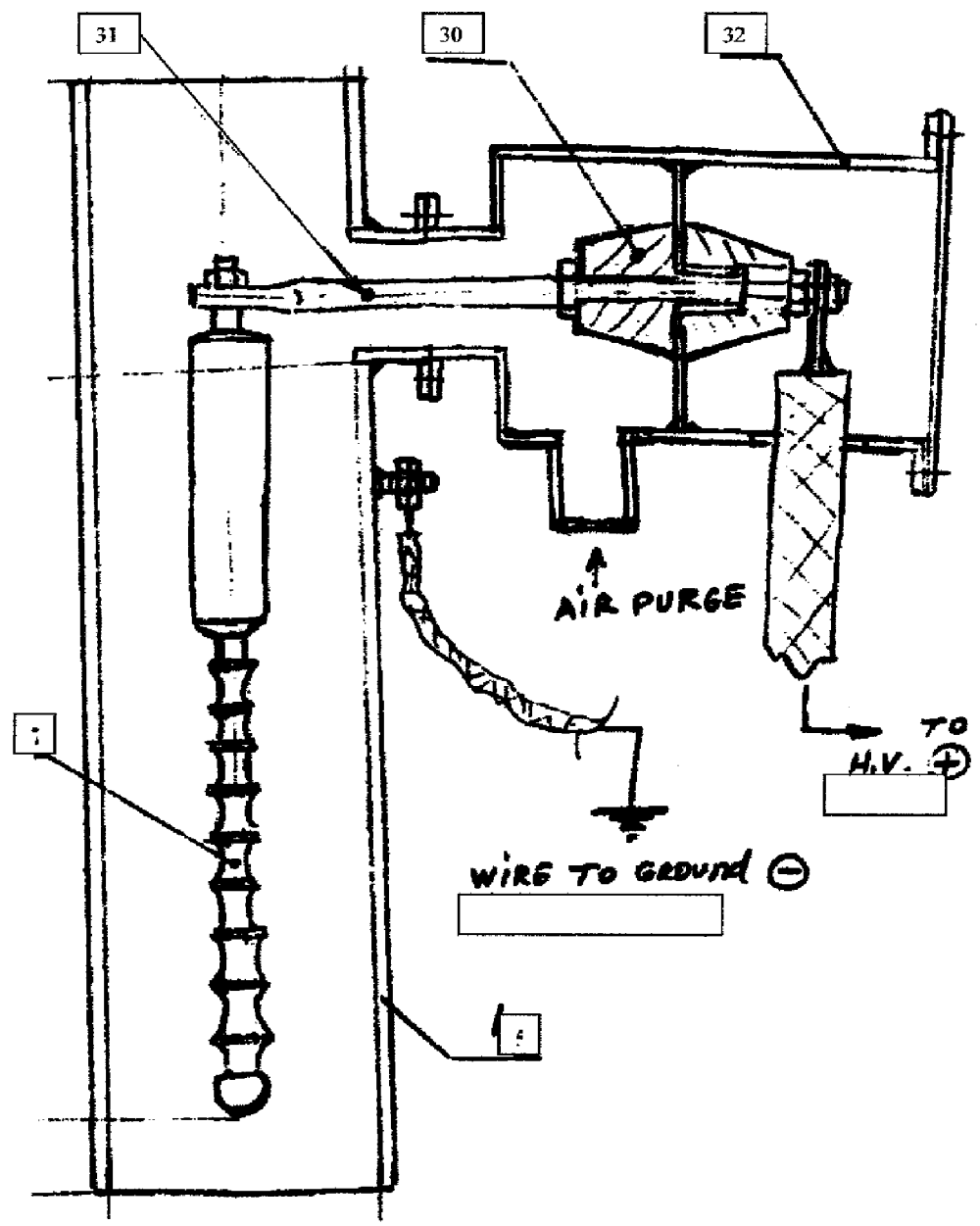
FIG. 3 is a cross-sectional view of a discharge electrode inserted along the axis of the collector electrode.

Modification 3: An accurately centered and well insulated discharge electrode 7 held by a bar 31 is inserted through the top of the upper chamber 19 of FIG. 2, as shown in FIG. 3.

To prevent shorting on the surface of a ceramic insulator 30 that is separating the positive and negative electrodes it is important to keep the insulator dean and dry, preferably in a dry chamber 32. The design shown on the extreme right of FIG. 3 serves to achieve this purpose. An air purge inlet, as shown in the drawing, helps prevent water condensation at the high-voltage connection.

The air sampling rate is varied by adjusting the voltage across the exhaust blower, as has been done with the inertial-type PHTLAAS of FIG. 1. Operation at reduced exhaust power helps to control mist formation and eliminate unwanted spark discharges. The voltage between electrodes 5 and 7 is varied by tuning an adjustable regulated High-Voltage DC Power Supply.

EXAMPLE 1:

For collection efficiency measurements, we use suspended 1-micron fluorescent beads obtained from Duke Scientific Corporation, Palo Alto, Calif. 94303. The fluorescent beads permit direct measurements with the aid of a fluorometer of the amounts of particles captured in the collection medium. The concentrations of particles in the sampled air are measured with the aid of a reference filter and their variations within out 3,000-liter test chamber are monitored with an APS [Aerodynamic Particle Sizer] instrument.

The described system was assembled, tested, and fine-tuned as follows:

1. The lower inlet portion of the WEP unit had a plastic inlet connected through a 3" diameter pipe to the ultrasonic humidifier and test chamber.

2. Using a redesigned rotor, the power required to circulate air through the WEP sampler to and from the test chamber at a rate of 510 l/min was only 8.4 watts [2 amps at 4.2 volts].

3. The following test procedure was worked out:

a. Run a dehumidifier for 10 minutes to reduce the relative humidity within the test chamber to <25%;

b. Circulate the contents of the test chamber through a HEPA filter for 10 minutes to reduce the particles count to a negligible value as measured with a TSI Model 3310 Aerodynamic Particle Sizer instrument.

c. With the fans in the test chamber turned on inject into the chamber about 1.2 ml of a standard suspension of 1.0-micron fluorescent latex particles through a nebulizer over a 5-minute period.

d. To start the sampling operation, prewet the walls of the collector electrode by running the ultrasonic humidifier at a maximum rate for 30 seconds with a low air-flow rate of only 120 l/min [drawing 0.74 amp at 1.17 volt or 0.8 watt of power] and a high-voltage power supply [HVPS] setting of 7,800±100 volts [drawing <0.1 mA or <0.8 watt].

e. Run the sampler for 6 minutes at an airflow rate of 510 l/min [drawing 8.4 watts as above], a reduced humidifier rate, and a HVPS setting of 12,000 volts [drawing an average current of 0.43 mA or 5.2 watts. A reference filter placed near the inlet of the WEP is also set to draw air at the rate of 20 l/min during this 6-minute time period simultaneously with the WEP sampler.

f. Flush down the walls of the collector tube by resetting the operating variables to those of the above step d. For best results, the narrow range of 7,800±100 volts for the HVPS setting should not be exceeded. Collect the first sample after 3.5 minutes of flushing and subsequent rinse samples at 5-minute intervals.

g. Compare the fluorescence of the test and rinse samples with that of the suspension obtained from the reference filter. The first results using the above procedure yielded collection efficiency values of 70±4% with a total collection volume of about 80 ml. A subsequent variation of that procedure yielded a collection efficiency of 87±6% with a collection volume of only 35 ml.

The afore-disclosed apparatus can be used in various ways depending on the hazards which are to be monitored or detected. The increased flow rate and collection efficiency with decreased power consumption will yield enhanced detection sensitivity and lesser weight of the resulting EP-based devices. The reported ability of wet EP systems to collect particles as small as 0.01 micron, and many gaseous species, such as dioxins/furans, at an efficiency of 99.9% will extend the demand for such devices even further by making them also applicable to the capture and detection of toxins and dry virus particles.

The high airflow rates and collection efficiencies which are achievable with wet EP technology not only for particles 1-10 microns in size but also for submicron particles render the PHTLAAS-EP applicable to ultra-sensitive detection of not only cellular pathogens, such as anthrax or tuberculosis bacilli, but also of the much smaller toxins and dry virus particles. The latter may pose a serious hazard following vaporization of the droplets in which they were originally dispersed. The capability to collect toxins and dry virus particles will therefore greatly strengthen the arsenal for defense against biological warfare agents.

The PHTLAAS-EP could be integrated into military field detectors, be helpful in other government activities, such as Treaty Verification, Domestic Preparedness, Demilitarization, and Homeland Defense, all of which will benefit from a smaller, lighter, more effective, and more energy-efficient collector which may capture not only single-cell pathogens but even dry virus particles and biological toxins. Civilian applications are also anticipated in many areas, such as medical monitoring, food packaging, and home inspection.

In the hands of first responders, the PHTLAAS-EP of this invention in conjunction with appropriate sensing means should provide the earliest possible post-exposure indication of a biological agent [BA] threat to facilitate diagnosis and treatment within the incubation period of most BAs, especially when used in conjunction with bio/non-bio or class-based detection that will indicate where to sample and when to analyze samples. Furthermore, civilian use of the technology for standard Industrial Hygiene practice should allow monitoring of HVAC systems for legionnaire's disease, molds, etc. There will now be obvious many variations and modifications of the aforedisclosed embodiments to persons skilled in the art. It will be obvious that similar approaches can apply to the detection and monitoring of illicit drugs and many hazardous substances, e.g., comprising cadmium, zinc, chromium, uranium, or compounds of these metals, miscellaneous carcinogens, and other toxic contaminants, that can be either absorbed directly in a suitable liquid extractant or solubilized therein from collected airborne particulates. All of these variations and modifications will remain within the scope of the invention if defined by the following claims:

We claim:

1. In wet electrostatic precipitation-based apparatus for detecting the presence of an airborne chemical or biological analyte, the improvement comprising: Providing an electrostatic precipitator to the wet electrostatic precipitation-based apparatus, wherein the electrostatic precipitator consists of A). A gas-and liquid-containing chamber; B). Means for introducing an analyte-free collection liquid into said chamber; and C). Means for rapidly sampling a volume of ambient air and transferring said analyte therefrom into said collection liquid, said sampling means consisting of: comprising an air intake means, an air venting means, and means for removing from said chamber an analyte-enriched collection liquid; wherein said volume of air passes through a horizontal air inlet and thence through a vertical electrically conductive collector electrode tube with means for applying and adjusting an electric field between said tube and a co-axial spiked wire- or rod-shaped discharge electrode, said collector tube and discharge electrode forming part of said chamber, wherein said electric field is high enough to effectuate a corona discharge so as to generate ionized particles that could be driven towards said collector electrode by an electric field, and wherein said removing means comprises means for feeding said enriched liquid to an appropriate detector or storing said liquid for subsequent analysis.

2. The apparatus of claim 1, comprising means for introducing a fine mist of droplets into said vertical conductive collector tube so as to cause full wetting of the inner surface of said tube by a liquid film.

3. The apparatus of claim 2, wherein said mist is generated by an ultrasonic humidifier.

4. The apparatus of claim 2, comprising means for generating and transmitting ultrasonic waves across the interface between said vertical conductive collector tube and said liquid film so as to help transfer particles or biological cells adhering to the tube surface from said surface into said film.

5. In a wet electrostatic precipitation-based method for detecting the presence of an airborne chemical or biological analyte, the improvement comprising the steps of: Providing an electrostatic precipitator to the wet electrostatic precipitation-based apparatus of claim 1, wherein the electrostatic precipitator which consists of: providing a gas- and liquid-containing means; introducing an analyte-free collection liquid into said containing means; rapidly passing a volume of ambient air through a sampling means forming part of said containing means and comprising an air intake means and an air venting means and transferring said analyte therefrom into said collection liquid by passing said volume of air through a substantially horizontal air inlet and thence through a vertical collector electrode tube while applying an electric field between said tube and a co-axial spiked wire- or rod-shaped discharge electrode, wherein said electric field is high enough to effectuate a corona discharge so as to generate ionized particles that could be driven towards said collector electrode by an electric field; and removing from said containing means an analyte-enriched collection liquid and either feeding it to an appropriate detector or storing it for subsequent analysis.

6. The method of claim 5, comprising the step of introducing a fine mist of droplets into the air stream passing through said vertical conductive collector tube so as to cause full wetting of the inner surface of said tube by a liquid film.

7. The method of claim 6, wherein said mist is generated ultrasonically.

8. The method of claim 6, comprising the step of generating and transmitting ultrasonic waves across the interface between said vertical conductive collector tube and said liquid film so as to help transfer particles or biological cells adhering to the tube surface from said surface into said film.

9. The apparatus of claim 1, wherein said vertical conductive collector electrode is tube-shaped with its inner surface electrically conducting.

10. The apparatus of claim 1, wherein said vertical conductive collector electrode is a metal or other electrically conductive material or comprises an electrically conductive coating or foil applied to the inner surface of a non-conductive tube.

11. The apparatus of claim 9, wherein said collector electrode has a roughened sandblasted inner surface.

12. A method of capturing for detection from a volume of air aerosolized particles as small as 0.01 micron in size which comprises passing said air through the wet electrostatic precipitation-based apparatus of claim 1.

13. The method of claim 12, wherein said particles are virus particles.

14. The method of claim 12, wherein said particles are toxin particles.

15. The apparatus of claim 1, comprising means for keeping said central wire-or rod- shaped discharge electrode at a high negative or positive potential, as much as 10 KV or higher, and wherein said vertical conductive collector electrode is tube-shaped with its inner surface electrically conducting, and said horizontal tubular air intake permits air to enter unimpeded at a high flow rate, possibly as high as 500 liters/minute or higher, with a minimal pressure drop.

16. The apparatus of claim 2, comprising means for assuring that said liquid film be at least 25 microns thick, so as to minimize collection losses due to captured particles adhering too firmly to the collector electrode.

17. The apparatus of claim 16, comprising means for forming said liquid film by dripping liquid from the top down a roughened, sandblasted, metal surface and/or by liquid droplets that are carried by the sampled air.

18. The apparatus of claim 16, comprising means for fine-tuning the thickness of said liquid film by adjustments of the power of an exhaust air blower and of the inter-electrode voltage and electric field distribution such as to assure that the introduced mist results wetting of the vertical conductive collector-electrode without causing unwanted spark discharges.

19. The apparatus of claim 1, wherein said electrodes and said electric field are so designed as to generate a sufficient corona to ionize a collection volume of 35 mL containing particles in the air stream and a sufficient electric field to deposit these particles with an efficiency of at least 87% at the vertical conductive collector electrode, and wherein the length and diameter of said vertical conductive collector electrode are such as to allow an adequate residence time for the particles to reach it rather than be carried away with the air stream.

20. The apparatus of claim 4, comprising means for operating the system in alternating dry and wet modes so as to cut down on evaporation losses during operation in the dry mode and thus reduce the water replenishment requirements and to also limit the occurrence of any power losses due to spark discharges to relatively brief wet wash-down periods.

\* \* \* \* \*